United States Patent
Zhang

(10) Patent No.: US 9,051,301 B2
(45) Date of Patent: Jun. 9, 2015

(54) CRYSTALLINE FORM OF A DRUG

(75) Inventor: Geoff G. Z. Zhang, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 11/229,922

(22) Filed: Sep. 19, 2005

(65) Prior Publication Data

US 2007/0123582 A1 May 31, 2007

Related U.S. Application Data

(60) Provisional application No. 60/611,122, filed on Sep. 17, 2004.

(51) Int. Cl.
C07D 207/12 (2006.01)
C07D 405/10 (2006.01)

(52) U.S. Cl.
CPC .................................. *C07D 405/10* (2013.01)

(58) Field of Classification Search
CPC .................................................... C07D 207/12
See application file for complete search history.

(56) References Cited

FOREIGN PATENT DOCUMENTS

WO 02/17912 7/2002

OTHER PUBLICATIONS

Chawla et al., "Challenges in Polymorphism of Pharmaceuticals", CRIPS vol. 5, No. 1, Jan.-Mar. 2004 (4 Pages).*
Newman et al., "Solid-state analysis of the active pharmaceutical ingredient in drug products", DDT vol. 8, No. 19, Oct. 2003, p. 898-905.*
Brittain et al. "Effects of pharmaceutical processing on drug polymorphs and solvates" in Polymorphism in Pharmaceutical Solids, vol. 95, p. 331-361.*
http://www.expresspharmaonline.com/20031023/edit02.shtml.*
Morley, et al., "Determination of the endothelein receptor receptor antagonist ABT-627 and related substances by high performance liquid chromatography", Journal of Pharmaceutical and Biomedical Analysis, vol. 19, No. 5, Apr. 1999; pp. 777-784.
Winn et al., "2,4-Diarylpyrrolidine-3-Carboxylic Acids—Potents ETA Selective Endothelin Receptor Antagonists 1. Discovery of A_127722". Journal of Medicinal Chemistry, American Chemical Society, vol. 39, No. 5, Mar. 1, 1996; pp. 1039-1048.
The PCT Search Report.

* cited by examiner

*Primary Examiner* — Sun Jae Yoo
(74) *Attorney, Agent, or Firm* — Michael J. Ward

(57) ABSTRACT

Atrasentan Hydrochloride Crystalline Form 3, compositions containing it and methods of treatment of diseases and inhibition of adverse physiological events using it are disclosed.

1 Claim, 1 Drawing Sheet

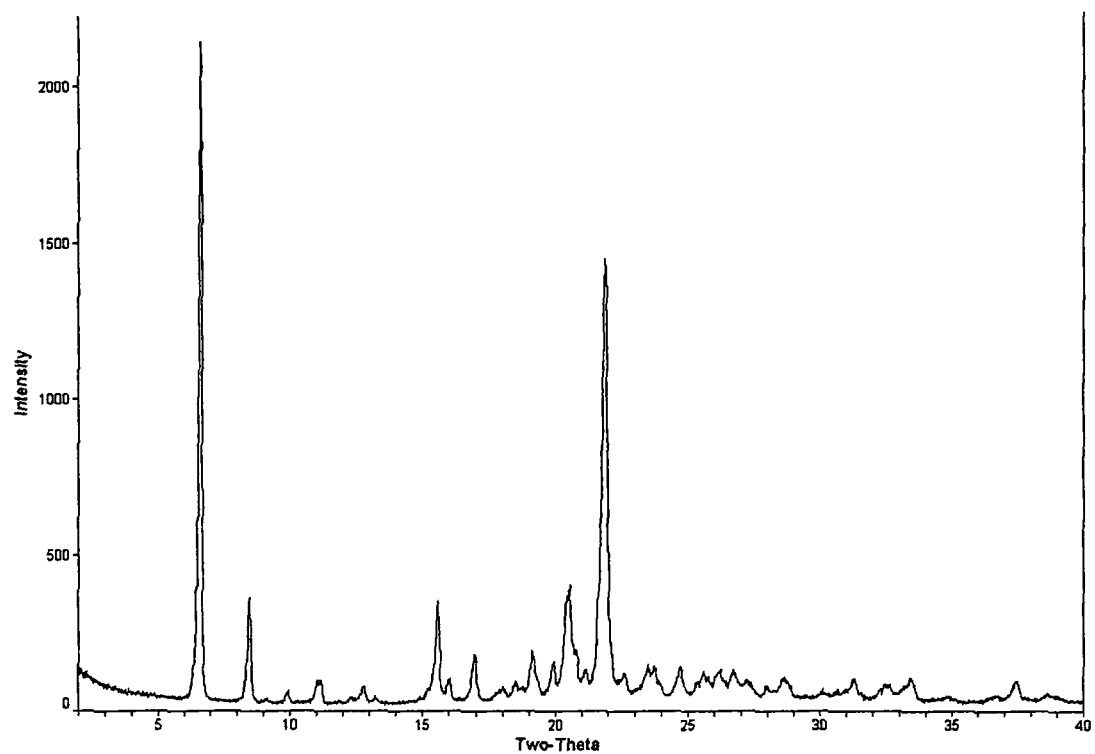

CRYSTALLINE FORM OF A DRUG

This application claims priority to U.S. Provisional Application Ser. No. 60/611,122, filed Sep. 17, 2004.

FIELD OF THE INVENTION

This invention pertains to a crystalline form of a drug, ways to make it, compositions containing it and methods of treatment of diseases and inhibition of adverse physiological events using it.

BACKGROUND OF THE INVENTION

Because the relationship between different crystalline forms of drugs may provide guidance for further development, there is an existing need in the chemical and therapeutic arts for identification of different crystalline forms of drugs and ways of reproducibly making them.

BRIEF DESCRIPTION OF THE FIGURE

FIG. 1 shows an experimental powder diffraction pattern of Atrasentan Hydrochloride Crystalline Form 3.

SUMMARY OF THE INVENTION

One embodiment of this invention pertains to Atrasentan Hydrochloride Crystalline Form 3 characterized, when measured at about 25° C. with Cu-Kα radiation, by a powder diffraction pattern with peaks having respective 2θ values of about 6.7° and 21.95° and at least one peak having a respective 2θ value of about 8.4°, 15.6°, 18.0°, 18.5°, 19.8° or 20.6°.

Another embodiment pertains to Atrasentan Hydrochloride Crystalline Form 3 having substantial crystalline purity and characterized, when measured at about 25° C. with Cu-Kα radiation, by a powder diffraction pattern with peaks having respective 2θ values of about 6.7° and 21.95° and at least one peak having a respective 2θ value of about 8.4°, 15.6°, 18.0°, 18.5°, 19.8° or 20.6°.

Still another embodiment pertains to Atrasentan Hydrochloride Crystalline Form 3 having substantial crystalline purity and substantial chemical purity and characterized, when measured at about 25° C. with Cu-Kα radiation, by a powder diffraction pattern with peaks having respective 2θ values of about 6.7° and 21.95° and at least one peak having a respective 2θ value of about 8.4°, 15.6°, 18.0°, 18.5°, 19.8° or 20.6°.

Still another embodiment pertains to Atrasentan Hydrochloride Crystalline Form 3 having substantial crystalline purity, substantial chemical purity and substantial diastereomeric purity and characterized, when measured at about 25° C. with Cu-Kα radiation, by a powder diffraction pattern with peaks having respective 2θ values of about 6.7° and 21.95° and at least one peak having a respective 2θ value of about 8.4°, 15.6°, 18.0°, 18.5°, 19.8° or 20.6°.

Still another embodiment pertains to compositions made with or comprising an excipient and Atrasentan Hydrochloride Crystalline Form 3.

Still another embodiment pertains to processes for making compositions made with or comprising an excipient and Atrasentan Hydrochloride Crystalline Form 3, the processes comprising the act of mixing the Atrasentan Hydrochloride Crystalline Form 3 and at least one of an encapsulating material, absorption accelerator, antioxidant, binder, buffer, coating agent, coloring agent, diluent, disintegrating agent, emulsifier, extender, filler, flavoring agent, humectant, lubricant, perfume, preservative, processing aid, releasing agent, shell excipient, sterilizing agent, sweetener, solubilizer or wetting agent.

Still another embodiment pertains to compositions made as described in the preceding embodiment.

Still another embodiment pertains to processes for making compositions made with or comprising an excipient and Atrasentan Hydrochloride Crystalline Form 3, the processes comprising the acts of mixing the Atrasentan Hydrochloride Crystalline Form 3 and at least one of polyethylene glycol 600, propylene gylcol, water, fractionated coconut oil, lecithin, ethanol and phosphatidylcholine and capsulating with FD&C No. 6, gelatin, glycerin, sorbitol, sorbitol anhydrides, mannitol and titanium dioxide.

Still another embodiment pertains to compositions made as described in the preceding embodiment.

Still another embodiment pertains to compositions made with or comprising Atrasentan Hydrochloride Crystalline Form 3 in combination with at least one of an encapsulating material, absorption accelerator, antioxidant, binder, buffer, coating agent, coloring agent, diluent, disintegrating agent, emulsifier, extender, filler, flavoring agent, humectant, lubricant, perfume, preservative, releasing agent, sterilizing agent, sweetener, solubilizer or wetting agent.

Still another embodiment pertains to compositions made with or comprising Atrasentan Hydrochloride Crystalline Form 3, ethanol, FD&C No. 6, fractionated coconut oil, gelatin, glycerin, lecithin, mannitol, phosphatidylcholine, polyethylene glycol 600, propylene gylcol, sorbitol, sorbitol anhydrides, titanium dioxide and water.

Still another embodiment pertains to compositions made with or comprising an excipient and Atrasentan Hydrochloride Crystalline Form 3 having about 0.01% to about 0.5% of at least one impurity selected from the group consisting of ethyl acetete, ethanol, (2R,3R,4S)-2-(4-methoxyphenyl)4-(1,3-benzodioxol-5-yl)-1-(N-(n-butyl)aminocarbonylmethyl)pyrrolidine-3-carboxylic acid, (2R,3R,4S)-2-(4-methoxyphenyl)-4-(1,3-benzodioxol-5-yl)-1-(N-(n-butyl)-N-ethyl)aminocarbonylmethyl)pyrrolidine-3-carboxylic acid, (2R,4S)-2-(4-methoxyphenyl)-4-(1,3-benzodioxol-5-yl)-1-(N,N-di(n-butyl)aminocarbonylmethyl)pyrrolidine, and ethyl (2R,3R,4S)-2-(4-methoxyphenyl)-4-(1,3-benzodioxol-5-yl)-1-(N,N-di(n-butyl)aminocarbonylmethyl)pyrrolidine-3-carboxylate.

Still another embodiment pertains to compositions made with or comprising ethanol, FD&C No. 6, fractionated coconut oil, gelatin, glycerin, lecithin, mannitol, phosphatidylcholine, polyethylene glycol 600, propylene gylcol, sorbitol, sorbitol anhydrides, titanium dioxide, water and Atrasentan Hydrochloride Crystalline Form 3 having about 0.01% to about 0.5% of at least one impurity selected from the group consisting of ethyl acetete, ethanol, (2R,3R,4S)-2-(4-methoxyphenyl)-4-(1,3-benzodioxol-5-yl)-1-(N-(n-butyl)aminocarbonylmethyl)pyrrolidine-3-carboxylic acid, (2R,3R,4S)-2-(4-methoxyphenyl)-4-(1,3-benzodioxol-5-yl)-1-(N-(n-butyl)-N-ethyl)aminocarbonylmethyl)pyrrolidine-3-carboxylic acid, (2R,4S)-2-(4-methoxyphenyl)-4-(1,3-benzodioxol-5-yl)-1-(N,N-di(n-butyl) aminocarbonylmethyl)pyrrolidine, and ethyl (2R,3R,4S)-2-(4-methoxyphenyl)-4-(1,3-benzodioxol-5-yl)-1-(N,N-di(n-butyl)aminocarbonylmethyl)pyrrolidine-3-carboxylate.

Still another embodiment pertains to mixtures comprising Atrasentan Hydrochloride Crystalline Form 1 and Atrasentan Hydrochloride Crystalline Form 3.

Still another embodiment pertains to mixtures comprising Atrasentan Hydrochloride Crystalline Form 3 and amorphous atrasentan hydrochloride.

Still another embodiment pertains to mixtures comprising Atrasentan Hydrochloride Crystalline Form 1, Atrasentan Hydrochloride Crystalline Form 3 and amorphous atrasentan hydrochloride.

Still another embodiment pertains to mixtures comprising Atrasentan Hydrochloride Crystalline Form 1 and Atrasentan Hydrochloride Crystalline Form 2 for use in preparing Atrasentan Hydrochloride Crystalline Form 3 having substantial crystalline purity.

Still another embodiment pertains to mixtures comprising Atrasentan Hydrochloride Crystalline Form 2 and Atrasentan Hydrochloride Crystalline Form 3 for use in preparing Atrasentan Hydrochloride Crystalline Form 3 having substantial crystalline purity.

Still another embodiment pertains to mixtures comprising Atrasentan Hydrochloride Crystalline Form 1, Atrasentan Hydrochloride Crystalline Form 2 and Atrasentan Hydrochloride Crystalline Form 3 for use in preparing Atrasentan Hydrochloride Crystalline Form 3 having substantial crystalline purity.

Still another embodiment pertains to mixtures comprising Atrasentan Hydrochloride Crystalline Form 2 and amorphous atrasentan hydrochloride for use in preparing Atrasentan Hydrochloride Crystalline Form 3 having substantial crystalline purity.

Still another embodiment pertains to mixtures comprising Atrasentan Hydrochloride Crystalline Form 1, Atrasentan Hydrochloride Crystalline Form 2 and amorphous atrasentan hydrochloride for use in preparing Atrasentan Hydrochloride Crystalline Form 3 having substantial crystalline purity.

Still another embodiment pertains to mixtures comprising Atrasentan Hydrochloride Crystalline Form 2, Atrasentan Hydrochloride Crystalline Form 3 and amorphous atrasentan hydrochloride for use in preparing Atrasentan Hydrochloride Crystalline Form 3 having substantial crystalline purity.

Still another embodiment pertains to mixtures comprising Atrasentan Hydrochloride Crystalline Form 1, Atrasentan Hydrochloride Crystalline Form 2, Atrasentan Hydrochloride Crystalline Form 3 and amorphous atrasentan hydrochloride for use in preparing Atrasentan Hydrochloride Crystalline Form 3 having substantial crystalline purity.

Still another embodiment pertains to methods for treating cancer, bone pain from bone cancer, bone pain from bone turnover, bone pain from net bone loss, fibrotic diseases, nociception, restinosis or stenosis in a human comprising administering thereto a therapeutically effective amount of Atrasentan Hydrochloride Crystalline Form 3.

Still another embodiment pertains to methods for treating cancer, bone pain from bone cancer, bone pain from bone turnover, bone pain from net bone loss, fibrotic diseases, nociception, restinosis or stenosis in a human comprising administering thereto a therapeutically effective amount of Atrasentan Hydrochloride Crystalline Form 3 and a therapeutically effective amount of at least one additional chemotherapeutic agent.

Still another embodiment pertains to methods for inhibiting bone metastases, metastatic growth, net bone loss or bone turnover in a human having kidney, lung, ovarian or prostate cancer that has metastasized to bone comprising administering thereto a therapeutically effective amount of Atrasentan Hydrochloride Crystalline Form 3.

Still another embodiment pertains to methods for inhibiting bone metastases, metastatic growth, net bone loss or bone turnover in a human having kidney, lung, ovarian or prostate cancer that has metastasized to bone comprising administering thereto a therapeutically effective amount of Atrasentan Hydrochloride Crystalline Form 3.

Still another embodiment pertains to methods for inhibiting bone metastases, metastatic growth, net bone loss or bone turnover in a human having kidney, lung, ovarian or prostate cancer that has metastasized to bone comprising administering thereto a therapeutically effective amount of Atrasentan Hydrochloride Crystalline Form 3 and a therapeutically effective amount of a compound that inhibits net bone loss.

Still another embodiment pertains to methods for preventing new metastatic growth in a human having kidney, lung, ovarian or prostate cancer that has metastasized to bone comprising administering thereto a therapeutically effective amount of Atrasentan Hydrochloride Crystalline Form 3.

Still another embodiment pertains to a process for making Atrasentan Hydrochloride Crystalline Form 3 having substantial crystalline purity, the process comprising the acts of:
  making and isolating or not isolating atrasentan or a solvate thereof;
  providing a mixture comprising the atrasentan or the solvate thereof and solvent, wherein the atrasentan is completely dissolved in the solvent;
  causing Atrasentan Hydrochloride Crystalline Form 3 to exist in the mixture or allowing Atrasentan Hydrochloride Crystalline Form 3 having substantial crystalline purity to develop in the mixture, the Atrasentan Hydrochloride Crystalline Form 3, when isolated and measured at about 25° C. with Cu-Kα radiation, characterized by a powder diffraction pattern with peaks having respective 2θ values of about 6.7° and 21.95° and at least one peak having a respective 2θ value of about 8.4°, 15.6°, 18.0°, 18.5°, 19.8° or 20.6°; and
  isolating the Atrasentan Hydrochloride Crystalline Form 3.

Still another embodiment pertains to a process for making Atrasentan Hydrochloride Crystalline Form 3 having substantial crystalline purity, the process comprising the acts of:
  making and isolating or not isolating atrasentan hydrochloride or a solvate thereof;
  providing a mixture comprising the atrasentan hydrochloride or the solvate thereof and solvent, wherein the atrasentan hydrochloride is completely dissolved in the solvent;
  causing Atrasentan Hydrochloride Crystalline Form 3 to exist in the mixture or allowing Atrasentan Hydrochloride Crystalline Form 3 having substantial crystalline purity to develop in the mixture, the Atrasentan Hydrochloride Crystalline Form 3, when isolated and measured at about 25° C. with Cu-Kα radiation, characterized by a powder diffraction pattern with peaks having respective 2θ values of about 6.7° and 21.95° and at least one peak having a respective 2θ value of about 8.4°, 15.6°, 18.0°, 18.5°, 19.8° or 20.6°; and
  isolating the Atrasentan Hydrochloride Crystalline Form 3.

Still another embodiment pertains to a process for making Atrasentan Hydrochloride Crystalline Form 3 having substantial crystalline purity, the process comprising the acts of:
  making and isolating or not isolating atrasentan or a solvate thereof;
  providing a mixture comprising the atrasentan or a solvate thereof solvent and HCl, wherein the solvent is supersaturated with the atrasentan hydrochloride thus formed;
  causing Atrasentan Hydrochloride Crystalline Form 3 to exist in the mixture or allowing Atrasentan Hydrochloride Crystalline Form 3 having substantial crystalline purity to develop in the mixture, the Atrasentan Hydrochloride Crystalline Form 3, when isolated and measured at about 25° C. with Cu-Kα radiation, characterized by a powder diffraction pattern with peaks having respective 2θ values of about 6.7° and 21.95° and at least one peak having a respective 2θ value of about 8.4°, 15.6°, 18.0°, 18.5°, 19.8° or 20.6°; and isolating the Atrasentan Hydrochloride Crystalline Form 3.

Still another embodiment pertains to a process for making Atrasentan Hydrochloride Crystalline Form 3 having substantial crystalline purity, the process comprising the acts of:

making and isolating or not isolating atrasentan hydrochloride or a solvate thereof;

providing a mixture comprising the atrasentan hydrochloride or the solvate thereof and solvent, wherein the solvent is supersaturated with the atrasentan hydrochloride;

causing Atrasentan Hydrochloride Crystalline Form 3 to exist in the mixture or allowing Atrasentan Hydrochloride Crystalline Form 3 having substantial crystalline purity to develop in the mixture, the Atrasentan Hydrochloride Crystalline Form 3, when isolated and measured at about 25° C. with Cu-Kα radiation, characterized by a powder diffraction pattern with peaks having respective 2θ values of about 6.7° and 21.95° and at least one peak having a respective 2θ value of about 8.4°, 15.6°, 18.0°, 18.5°, 19.8° or 20.6°; and isolating the Atrasentan Hydrochloride Crystalline Form 3.

Still another embodiment pertains to a process for making Atrasentan Hydrochloride Crystalline Form 3 having substantial crystalline purity, the process comprising:

making and isolating or not isolating atrasentan hydrochloride or a solvate thereof;

providing a mixture comprising the atrasentan hydrochloride and solvent, wherein the atrasentan hydrochloride is partially soluble in the solvent;

allowing Atrasentan Hydrochloride Crystalline Form 3 having substantial crystalline purity to develop in the mixture, the Atrasentan Hydrochloride Crystalline Form 3, when isolated and measured at about 25° C. with Cu-Kα radiation, characterized by a powder diffraction pattern with peaks having respective 2θ values of about 6.7° and 21.95° and at least one peak having a respective 2θ value of about 8.4°, 15.6°, 18.0°, 18.5°, 19.8° or 20.6°; and isolating the Atrasentan Hydrochloride Crystalline Form 3.

Still another embodiment pertains to a process for making Atrasentan Hydrochloride Crystalline Form 3 having substantial crystalline purity, the process comprising:

making and isolating or not isolating atrasentan hydrochloride or a solvate thereof;

providing a mixture comprising the atrasentan hydrochloride and solvent at about 40° C. or higher than 40° C., wherein in which the atrasentan hydrochloride is partially soluble in the solvent;

allowing Atrasentan Hydrochloride Crystalline Form 3 having substantial crystalline purity to develop in the mixture; and isolating the Atrasentan Hydrochloride Crystalline Form 3.

Still another embodiment pertains to a process for making Atrasentan Hydrochloride Crystalline Form 3 having substantial crystalline purity, the process comprising:

providing a mixture comprising atrasentan hydrochloride and solvent at about 40° C. or higher than 40° C., wherein the atrasentan hydrochloride is partially soluble in the solvent;

allowing Atrasentan Hydrochloride Crystalline Form 3 having substantial crystalline purity to develop in the mixture; and isolating the Atrasentan Hydrochloride Crystalline Form 3.

In a process for making Atrasentan Hydrochloride Crystalline Form 3 by deprotection of carboxylic acid-protected cis,cis-2-(4-methoxyphenyl)-4-(1,3-benzodioxol-5-yl)pyrrolidine-3-carboxylic acid, carboxylic acid-protected trans,trans-2-(4-methoxyphenyl)-4-(1,3-benzodioxol-5-yl)pyrrolidine-3-carboxylic acid or carboxylic acid-protected atrasentan with subsequent crystallization or recrystallization of atrasentan hydrochloride to the Atrasentan Hydrochloride Crystalline Form 3, the process comprising direct crystallization of Atrasentan Hydrochloride Crystalline Form 3 from a solid, semisolid or syrup having therewith at least one residual solvent from the carboxylic acid deprotection reaction.

In a process for making Atrasentan Hydrochloride Crystalline Form 3 by deprotection of carboxylic acid-protected cis,cis-2-(4-methoxyphenyl)-4-(1,3-benzodioxol-5-yl)pyrrolidine-3-carboxylic acid, carboxylic acid-protected trans,trans-2-(4-methoxyphenyl)-4-(1,3-benzodioxol-5-yl)pyrrolidine-3-carboxylic acid or carboxylic acid-protected atrasentan with subsequent crystallization or recrystallization of atrasentan hydrochloride to the Atrasentan Hydrochloride Crystalline Form 3, the process comprising direct crystallization of Atrasentan Hydrochloride Crystalline Form 3 from a solid having therewith at least one residual solvent from the group consisting of water, tetrahydrofuran, ethyl acetate, ethanol and hexanes from the carboxylic acid deprotection reaction.

In a process for making Atrasentan Hydrochloride Crystalline Form 3 by deprotection of carboxylic acid-protected atrasentan and crystallization or recrystallization of atrasentan hydrochloride to the Atrasentan Hydrochloride Crystalline Form 3, the process comprising direct crystallization of Atrasentan Hydrochloride Crystalline Form 3 from a solid, semisolid or syrup having therewith at least one residual solvent selected from the group consisting of water, tetrahydrofuran, ethyl acetate and ethanol from the carboxylic acid deprotection reaction.

Still another embodiment pertains to Atrasentan Hydrochloride Crystalline Form 3 prepared as described in any of the preceding process embodiments.

Still another embodiment pertains to methods of treating bone pain from bone cancer, bone pain from bone turnover, bone pain from net bone loss, fibrotic diseases, nociception, restinosis or stenosis in a human comprising administering thereto a therapeutically effective amount of Atrasentan Hydrochloride Crystalline Form 3 prepared as described in any of the preceding process embodiments.

Still another embodiment pertains to methods of inhibiting bone metastases, metastatic growth, net bone loss or bone turnover in a human having kidney, lung, ovarian or prostate cancer that has metastasized to bone comprising administering thereto a therapeutically effective amount of Atrasentan Hydrochloride Crystalline Form 3 prepared as described in any of the preceding process embodiments.

Still another embodiment pertains to methods of inhibiting bone metastases, metastatic growth, net bone loss or bone turnover in a human having kidney, lung, ovarian or prostate cancer that has metastasized to bone comprising administering thereto a therapeutically effective amount of Atrasentan Hydrochloride Crystalline Form 3, prepared as described in any of the preceding process embodiments, and a therapeutically effective amount of an agent that inhibits net bone loss.

Still another embodiment pertains to methods of preventing new metastatic growth in a human having kidney, lung, ovarian or prostate cancer that has metastasized to bone comprising administering thereto a therapeutically effective amount of Atrasentan Hydrochloride Crystalline Form 3 prepared as described in any of the preceding process embodiments.

DETAILED DESCRIPTION OF THE INVENTION

This invention pertains to discovery of Atrasentan Hydrochloride Crystalline Form 3, ways to make it having substantial crystalline, chemical and diastereomeric purity, ways to characterize it, compositions containing it and methods of treatment of diseases and inhibition of adverse physiological events using it.

Moieties herein may be represented by capital letters with numerical superscripts and are specifically embodied. For example, —CH(◂—R$^3$)CH( ⋯ᵗᵗ R$^4$)CH( ◂—R$^5$)— is represented by R$^1$ and R$^2$ together, and 1,3-benzodioxol-5-yl, $CO_2H$ and 4-methoxyphenyl specifically embody R$^3$, R$^4$ and R$^5$, respectively. R$^3$ is attached to a carbon atom assigned the S configuration, R$^4$ is attached to a carbon atom assigned the R configuration and R$^5$ is attached to a carbon atom assigned the R configuration. Accordingly, R$^1$ and R$^2$ together may also be written as —$^{(S)}$CH( ◂—R$^3$)$^{(R)}$CH( ⋯ᵗᵗ R$^4$)$^{(R)}$—CH( ◂—R$^5$)—. Atrasentan hydrochloride is also referred to herein by the name (2R,3R,4S)-(+)-2-(4-methoxyphenyl)-4-(1,3-benzodioxol-5-yl)-1-(N,N-di(n-butyl)aminocarbonylmethyl)pyrrolidine-3-carboxylic acid.

The stereochemical assignments "R" and "S" are as defined by IUPAC 1974 Recommendations for Section E, Fundamental Stereochemistry, Pure Appl. Chem. (1976) 45, 13-10.

The term "amorphous," as used herein, means a supercooled liquid or a viscous liquid which looks like a solid but does not have a regularly repeating arrangement of molecules that is maintained over a long range and does not have a melting point but rather softens or flows above its glass transition temperature.

The term "anti-solvent," as used herein, means a solvent in which a compound is substantially insoluble.

The term "Atrasentan Hydrochloride Crystalline Form 3," as used herein, means the most thermodynamically crystalline form of atrasentan hydrochloride at or above about 40° C.

The term "chemical purity," as used herein, means percentage of a particular compound in a sample. A sample of Atrasentan Hydrochloride Crystalline Form 3 may contain, for example, atrasentan, water, ethyl acetate, ethanol, R$^1$CH$_2$N(R$^2$)CH$_2$C(O)N(H)((CH$_2$)$_3$CH$_3$) or the hydrochloride salt thereof, R$^1$CH$_2$N(R$^2$)CH$_2$C(O)N(CH$_2$CH$_3$) ((CH$_2$)$_3$CH$_3$) or the hydrochloride salt thereof, R$^{1a}$CH$_2$N(R$^{2a}$)CH$_2$C(O)N((CH$_2$)$_3$CH$_3$)$_2$ or the hydrochloride salt thereof, wherein R$^{1a}$ and R$^{2a}$ are together and are —CH( ◂—R$^3$)CH$_2$CH( ◂—R$^5$)—, R$^{1b}$CH$_2$N(R$^{2b}$)CH$_2$C(O)N((CH$_2$)$_3$CH$_3$)$_2$ or the hydrochloride salt thereof, wherein R$^{1b}$ and R$^{2b}$ together and are —CH( ◂—R$^3$)CH( ⋯ᵗᵗ R$^{4a}$)—CH( ◂—R$^5$)—, wherein R$^{4a}$ is $CO_2CH_2CH_3$, or mixtures thereof. Accordingly, Atrasentan Hydrochloride Crystalline Form 3 and compositions comprising or made from Atrasentan Hydrochloride Crystalline Form 3 may contain at least one impurity selected from the group consisting of water, ethyl acetate, ethanol, (2R,3R,4S)-2-(4-methoxyphenyl)-4-(1,3-benzodioxol-5-yl)-1-(N-(n-butyl)aminocarbonylmethyl)pyrrolidine-3-carboxylic acid, (2R,3R,4S)-2-(4-methoxyphenyl)-4-(1,3-benzodioxol-5-yl)-1-(N-(n-butyl)-N-ethyl)aminocarbonylmethyl)pyrrolidine-3-carboxylic acid(2R,4S)-2-(4-methoxyphenyl)-4-(1,3-benzodioxol-5-yl)-1-(N,N-di(n-butyl)aminocarbonylmethyl)pyrrolidine, and ethyl (2R,3R,4S)-2-(4-methoxyphenyl)-4-(1,3-benzodioxol-5-yl)-1-(N,N-di(n-butyl)aminocarbonylmethyl)pyrrolidine-3-carboxylate.

The term "crystalline," as used herein, means having a regularly repeating arrangement of molecules or external face planes.

The term "crystalline purity," as used herein, means percentage of Atrasentan Hydrochloride Crystalline Form 3 in a sample that may contain amorphous atrasentan hydrochloride, at least one crystalline form of atrasentan hydrochloride other than Atrasentan Hydrochloride Crystalline Form 3 or mixtures thereof.

The term "diastereomeric excess," as used herein, means amount of one diastereomer of a compound in a mixture which may have other diastereomers of the same compound in the mixture.

The term "essentially without," as used herein in reference to peaks in a powder diffraction pattern, means peaks having intensities below about 5%, preferably below about 3%, more preferably below about 1%, and still more preferably below about 0.1%.

The term "isolating" as used herein, means separating a compound from a solvent, anti-solvent, or a mixture of solvent and anti-solvent to provide a solid, semisolid or syrup. This is typically accomplished by means such as centrifugation, filtration with or without vacuum, filtration under positive pressure, distillation, evaporation or a combination thereof. Isolating may or may not be accompanied by purifying during which the chemical, chiral or chemical and chiral purity of the isolate is increased. Purifying is typically conducted by means such as crystallization, distillation, extraction, filtration through acidic, basic or neutral alumina, filtration through acidic, basic or neutral charcoal, column chromatography on a column packed with a chiral stationary phase, filtration through a porous paper, plastic or glass barrier, column chromatography on silica gel, ion exchange chromatography, recrystallization, normal-phase high performance liquid chromatography, reverse-phase high performance liquid chromatography, trituration and the like.

The term "miscible," as used herein, means capable of combining without separation of phases.

The term "solvate," as used herein, means having on a surface, in a lattice or on a surface and in a lattice, a solvent such as water, acetic acid, acetone, acetonitrile, benzene, chloroform, carbon tetrachloride, dichloromethane, dimethylsulfoxide, 1,4-dioxane, ethanol, ethyl acetate, butanol, tert-butanol, N,N-dimethylacetamide, N,N-dimethylformamide, formamide, formic acid, heptane, hexane, isopropanol, methanol, methyl ethyl ketone, 1-methyl-2-pyrrolidinone, mesitylene, nitromethane, polyethylene glycol, propanol, 2-propanone, pyridine, tetrahydrofuran, toluene, xylene, mixtures thereof and the like. A specific example of a solvate is a hydrate, wherein the solvent on the surface, in the lattice or on the surface and in the lattice, is water. Hydrates may or may not have solvents other than water on the surface, in the lattice or on the surface and in the lattice of a substance.

The term "substantial chemical purity," as used herein, means about 95% chemical purity, preferably about 97% chemical purity, more preferably about 98% chemical purity, and most preferably about 100% chemical purity.

The term "substantial crystalline purity," as used herein, means at least about 95% crystalline purity, preferably about 97% crystalline purity, more preferably about 99% crystalline purity, and most preferably about 99.9% crystalline purity.

The term "substantial diastereomeric purity," as used herein, means diastereomeric excess greater than about 95%, preferably greater than about 97%, more preferably greater than about 99%, and most preferably about 100%, wherein impurities are one or more of seven other diastereomers resulting from arrangement of substituents for R$^1$ and R$^2$ together, which diastereomers are compounds having formula R$^1$CH$_2$N(R$^2$)CH$_2$C(O)N((CH$_2$)$_3$CH$_3$)$_2$.HCl wherein R$^1$ and R$^2$ together are —$^{(S)}$CH( ◂—R$^3$)$^{(S)}$CH( ⋯ᵗᵗ R$^4$)$^{(S)}$—

CH($\rightarrow$R$^5$)—, —$^{(R)}$CH( $\rightarrow$R$^3$)$^{(R)}$CH( ⋯⋯R$^4$)$^{(R)}$
CH($\rightarrow$R$^5$)—, —$^{(R)}$CH( $\rightarrow$R$^3$)$^{(S)}$—CH( ⋯⋯R$^4$)$^{(S)}$
CH($\rightarrow$R$^5$)—, —$^{(R)}$CH( $\rightarrow$R$^3$)—$^{(S)}$CH( ⋯⋯R$^4$)$^{(R)}$
CH($\rightarrow$R$^5$)—, —$^{(S)}$CH( $\rightarrow$R$^3$)$^{(R)}$CH( ⋯⋯R$^4$)$^{(S)}$
CH($\rightarrow$R$^5$)—, —$^{(S)}$CH( $\rightarrow$R$^3$)$^{(S)}$CH( ⋯⋯R$^4$)$^{(R)}$—
CH($\rightarrow$R$^5$)—, —$^{(R)}$CH( $\rightarrow$R$^3$)$^{(R)}$CH( ⋯⋯R$^4$)$^{(S)}$—
CH($\rightarrow$R$^5$)— or mixtures thereof.

The term "supersaturated," as used herein, means having a compound in a solvent in which it is completely dissolved at a certain temperature but at which the solubility of the compound in the solvent at that certain temperature is exceeded.

Unless stated otherwise, percentages stated throughout this specification are weight/weight (w/w) percentages.

Mixtures comprising atrasentan hydrochloride and solvent may or may not have chemical and diastereomeric impurities, which, if present, may be completely soluble, partially soluble or essentially insoluble in the solvent. The level of chemical or diastereomeric impurity in the mixture may be lowered before or during isolation of Atrasentan Hydrochloride Crystalline Form 3 by means such as distillation, extraction, filtration through acidic, basic or neutral alumina, filtration through acidic, basic or neutral charcoal, column chromatography on a column packed with a chiral stationary phase, filtration through a porous paper, plastic or glass barrier, column chromatography on silica gel, ion exchange chromatography, recrystallization, normal-phase high performance liquid chromatography, reverse-phase high performance liquid chromatography, trituration and the like.

Causing Atrasentan Hydrochloride Crystalline Form 3 to exist in a mixture comprising atrasentan hydrochloride and solvent, wherein the atrasentan hydrochloride is completely dissolved in the solvent, is nucleation. In a preferred embodiment for the practice of this invention, nucleation of Atrasentan Hydrochloride Crystalline Form 3 is made to occur in a solvent which is supersaturated with atrasentan hydrochloride.

Mixtures of atrasentan hydrochloride and solvent, wherein the atrasentan hydrochloride is completely or partially dissolved in the solvent may be prepared from a crystalline atrasentan hydrochloride, amorphous atrasentan hydrochloride or a mixture thereof, wherein the crystalline atrasentan hydrochloride and amorphous atrasentan hydrochloride may or may not be substantially chemically, diastereomerically or chemically and diastereomerically pure. Examples of crystalline atrasentan hydrochloride include, but are not limited to, Atrasentan Hydrochloride Crystalline Form 1, Atrasentan Hydrochloride Crystalline Form 2, Atrasentan Hydrochloride Crystalline Form 3, and mixtures thereof.

Preparation and properties of Atrasentan Hydrochloride Crystalline Form 1 are disclosed in commonly-owned U.S. application Ser. No. 11/229,892.

Preparation and properties of Atrasentan Hydrochloride Crystalline Form 2 are disclosed in commonly-owned U.S. application Ser. No. 11/230,043.

Preparation and properties of amorphous atrasentan hydrochloride are disclosed in commonly-owned U.S. application Ser. No. 11/229,894.

For the practice of this invention, nucleation may be made to occur in a solution by techniques that are well-known to those skilled in the art such as, for example, solvent removal, temperature change, solvent-miscible anti-solvent addition, solvent-immiscible anti-solvent addition, seed crystal addition of Atrasentan Hydrochloride Crystalline Form 3, chafing or scratching the interior of the container, preferably a glass container with a glass rod or a glass bead or beads, or by a combination thereof.

It is meant to be understood that, because many solvents and anti-solvents contain 3 0 impurities, the level of impurities in solvents and anti-solvents for the practice of this invention, if present, are at a low enough concentration that they do not interfere with the intended use of the solvent in which they are present.

The solubility (in mg/mL) of Atrasentan Hydrochloride Crystalline Forms 1, 2 and 3 in 1,4-dioxane at 25° C. (n=3) is shown in TABLE 1.

TABLE 1

| Form 1 | 35.60 ± 1.82 |
| Form 2 | 16.66 ± 0.22 |
| Form 3 | 16.53 ± 0.22 |

Atrasentan and solvates thereof and atrasentan hydrochloride and solvates thereof can be made by synthetic chemical processes, an example of which is shown hereinbelow. It is meant to be understood that the order of the steps in the processes may be varied, that reagents, solvents and reaction conditions may be substituted for those specifically mentioned, and that moieties succeptable to undesired reaction may be protected and deprotected, as necessary. For example, they can be made by reacting 5-((E)-2-nitroethenyl)-1,3-benzodioxole, a compound having formula (1)

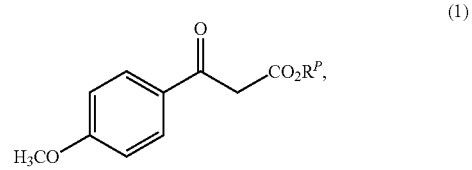

(1)

wherein R$^P$ is a carboxyl protecting group, and a first base to provide a compound having formula (2)

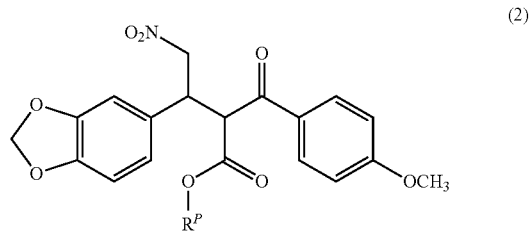

(2)

and isolating or not isolating the compound having formula (2);

reacting the compound having formula (2) and a hydrogenation catalyst to provide a compound having formula (3) with the relative stereochemistry shown therefor

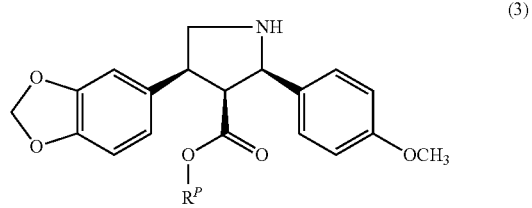

(3)

and isolating or not isolating the compound having formula (3);

reacting the compound having formula (3) and a second base to provide a compound having formula (4) with the relative stereochemistry shown therefor

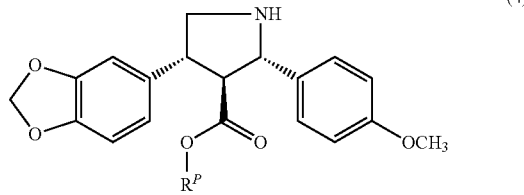

and not isolating the compound having formula (4) or isolating the compound having formula (4) and reacting the same and a chiral auxiliary and isolating the compound having formula (4) with the absolute stereochemistry shown therefor;

reacting the compound having formula (4), a third base and a compound having formula (5) $X^1CH_2C(O)N((CH_2)_3CH_3)_2$, wherein $X^1$ is Cl, Br, I or $OSO_2R^8$, wherein $R^8$ is methyl, ethyl or $R^9$, wherein $R^9$ is phenyl that is unsubstituted or substituted with one of $CH_3$, $OCH_3$, Cl or Br, and isolating or not isolating a compound having formula (5) with the absolute stereochemistry shown therefor

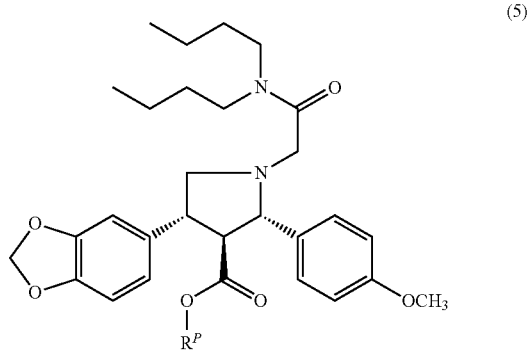

or isolating the compound having formula (5) with the relative stereochemistry shown therefor and reacting the same and a chiral auxiliary and isolating the compound having formula (5) with the absolute stereochemistry shown therefor; and reacting the compound having formula (5) and a carboxyl deprotecting agent and isolating or not isolating the atrasentan or the solvate thereof or the atrasentan hydrochloride or the solvate thereof.

The term "absolute stereochemistry," as used herein means the orientation of substituents on a compound having substantial diastereomeric purity.

The term "$C_1$-alkyl," as used herein, means methyl.
The term "$C_2$-alkyl," as used herein, means ethyl.
The term "$C_3$-alkyl," as used herein, means prop-1-yl and prop-2-yl (isopropyl).
The term "$C_4$-alkyl," as used herein, means but-1-yl, but-2-yl, 2-methylprop-1-yl and 2-methylprop-2-yl (tert-butyl).
The term "$C_5$-alkyl," as used herein, means 2,2-dimethylprop-1-yl (neo-pentyl), 2-methylbut-1-yl, 2-methylbut-2-yl, 3-methylbut-1-yl, 3-methylbut-2-yl, pent-1-yl, pent-2-yl and pent-3-yl.

The term "$C_6$-alkyl," as used herein, means 2,2-dimethylbut-1-yl, 2,3-dimethylbut-1-yl, 2,3-dimethylbut-2-yl, 3,3-dimethylbut-1-yl, 3,3-dimethylbut-2-yl, 2-ethylbut-1-yl, hex-1-yl, hex-2-yl, hex-3-yl, 2-methylpent-1-yl, 2-methylpent-2-yl, 2-methylpent-3-yl, 3-methylpent-1-yl, 3-methylpent-2-yl, 3-methylpent-3-yl, 4-methylpent-1-yl and 4-methylpent-2-yl.

The term "carboxyl deprotecting agent," as used herein means any reagent that can remove a carboxyl protecting group from a C(O)OH moiety. The nature of the carboxyl protecting group will determine its means of removal. The most general carboxyl deprotecting agents are sodium hydroxide, potassium hydroxide, lithium hydroxide, calcium hydroxide and barium hydroxide.

The term "carboxyl protecting group," as used herein means any moiety that can be attached to a C(O)OH moiety to make it less susceptable to undesired reaction during synthesis. Specific examples of carboxyl protecting groups include, bur are not limited to, phenyl, naphthyl, furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl, 1,2,3-triazolyl acetoxymethyl, allyl, benzoylmethyl, benzyloxymethyl, tert-butyldiphenylsilyl, diphenylmethyl, cyclobutyl, cyclohexyl, cyclopentyl, cyclopropyl, diphenylmethylsilyl, paramethoxybenzyl, methoxymethyl, methoxyethoxymethyl, methylthiomethyl, para-nitrobenzyl, phenyl, 2,2,2-trichloroethyl, triethylsilyl, 2-(trimethylsilyl)ethyl, 2-(trimethylsilyl)ethoxymethyl, triphenylmethyl or $C_1$-alkyl, $C_2$-alkyl, $C_3$-alkyl, $C_4$-alkyl, $C_5$-alkyl or $C_6$-alkyl, each of which is unsubstituted or substituted with phenyl, naphthyl, furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl, 1,2,3-triazolyl and the like.

The term "chiral auxiliary," as used herein, means a compound that can be reversibly attached ionically (to make a salt therewith) or reversibly attached covalently (to couple therewith) to a compound having relative stereochemistry so that a diastereomer of the compound having absolute stereochemistry with substantial diastereomeric purity can be isolated. The term "chiral auxiliary," can also mean a chiral stationery phase of a chiral chromatography column. Examples of chiral auxiliaries that are useful for the practice of this invention are compounds having at least one chiral center with about 99.5% to about 99.9% optical purity at those centers and at least one C(O)OH or $SO_2H$ moiety.

The term "first base," as used herein means sodium methoxide, sodium ethoxide, sodium tert-amylate, sodium tert-butoxide, potassium methoxide, potassium ethoxide, sodium tert-amylate, sodium tert-butoxide and the like.

The term "hydrogenation catalyst," as used herein means Raney nickel, palladium on carbon, platinum on carbon, palladium(II) hydroxide, palladium(II) hydroxide on carbon and the like.

The term "relative stereochemistry," as used herein means as used herein means the orientation of substituents on a compound in relation to other substituents on the same molecule.

The term "second base," as used herein means sodium methoxide, sodium ethoxide, sodium tert-amylate, sodium tert-butoxide, potassium methoxide, potassium ethoxide, sodium tert-amylate, sodium tert-butoxide, 1,8-diazabicylco[5.4.0]undec-7-ene, 1,5-diazabicylco[4.3.0]non-5-ene, and the like.

The term "third base," as used herein means calcium carbonate, sodium bicarbonate, sodium carbonate, potassium arbonate, lithium carbonate, triethylamine, diisopropylethylamine and the like.

The following examples are presented to provide what is believed to be the most useful and readily understood description of procedures and conceptual aspects of this invention.

EXAMPLE 1

A mixture of bromoacetyl bromide (72.3 mL) in toluene (500 mL) at 0° C. was treated with dibutylamine (280 mL) in toluene (220 mL) while keeping the solution temperature below 10° C., stirred at 0° C. for 15 minutes, treated with 2.5% aqueous phosphoric acid (500 mL) and warmed to 25° C. The organic layer was isolated, washed with water (500 mL) and concentrated to provide the product as a solution in toluene.

EXAMPLE 2

5-((E)-2-nitroethenyl)-1,3-benzodioxole 3,4-methylenedioxybenzaldehyde (15.55 Kg) was treated sequentially with ammonium acetate (13.4 Kg,), acetic acid (45.2 Kg) and nitromethane (18.4 Kg), warmed to 70° C., stirred for 30 minutes, warmed to 80° C., stirred for 10 hours, cooled to 10° C. and filtered. The filtrant was washed with acetic acid (2×8 Kg) and water (2×90 Kg) and dried under a nitrogen stream then in under vacuum at 50 ° C. for 2 days.

EXAMPLE 3 ethyl 3-(4-methoxyphenyl-3-oxopropanoate

A mixture of potassium tert-amylate (50.8 Kg) in toluene (15.2 Kg) at 5° C. was treated with 4-methoxyacetophenone (6.755 Kg) and diethyl carbonate (6.4 Kg) in toluene over 1 hour while keeping the solution temperature below 10° C., warmed to 60° C. for 8 hours, cooled to 20° C. and treated with acetic acid (8 Kg) and water (90Kg) over 30 minutes while keeping the solution temperature below 20° C. The organic layer was isolated, washed with 5% aqueous sodium bicarbonate (41 Kg) and concentrated at 50° C. to 14.65 Kg.

EXAMPLE 4 ethyl 2-(4-methoxybenzoyl)-4-nitromethyl-3-(1,3-benzodioxol-5-yl)butyrate

A mixture of EXAMPLE 3 (7.5 Kg) in THF (56 Kg) was treated with EXAMPLE 3 (8.4 Kg), cooled to 17° C., treated with sodium ethoxide (6.4 g), stirred for 30 minutes, treated with more sodium ethoxide (6.4 g), stirred at 25° C. until HPLC shows less than 1 area % ketoester remaining and concentrated to 32.2 Kg.

EXAMPLE 5 ethyl cis,cis-2-(4-methoxyphenyl)-4-(1,3-benzodioxol-5-yl)pyrrolidine-3-carboxylate Raney nickel (20 g), from which the water had been decanted, was treated sequentially with THF (20 mL), EXAMPLE 4 (40.82 g), and acetic acid (2.75 mL). The mixture was stirred under hydrogen (60 psi) until hydrogen uptake slowed, treated with trifluoroacetic acid, stirred under hydrogen (200 psi) until HPLC shows no residual imine and less than 2% nitrone and filtered with a methanol (100 mL) wash. The filtrate, which contained 13.3 g of EXAMPLE 5, was concentrated with THF (200 mL) addition to 100 mL, neutralized with 2N aqueous NaOH (50 mL), diluted with water (200 mL), and extracted with ethyl acetate (2×100 mL). The extract was used in the next step.

EXAMPLE 6 ethyl trans,trans-2-(4-methoxyphenyl)-4-(1,3-benzodioxol-5-yl)pyrrolidine-3-carboxylate Example 501E (38.1 g) was concentrated with ethanol (200 mL) addition to 100 mL, treated with sodium ethoxide (3.4 g), heated to 75° C., cooled to 25° C. when HPLC showed less than 3% of EXAMPLE 1E and concentrated. The concentrate was mixed with isopropyl acetate (400 mL), washed with water (2×150 mL) and extracted with 0.25 M phosphoric acid (2×400 mL). The extract was mixed with ethyl acetate (200 mL) and neutralized to pH 7 with sodium bicarbonate (21 g), and the organic layer was isolated.

EXAMPLE 7 ethyl (2R,3R,4S)-(+)-2-(4-methoxyphenyl)-4-(1,3-benzodioxol-5-yl)pyrrolidine-3-carboxylate, (S)-(+) mandelate EXAMPLE 501F was concentrated with acetonitrile (100 mL) addition to 50 mL, treated with (S)-(+)-mandelic acid (2.06 g), stirred until a solution formed, stirred for 16 hours, cooled to 0° C., stirred for 5 hours and filtered. The filtrant was dried at 50° C. under a nitrogen stream for 1 day. The purity of the product was determined by chiral HPLC using Chiralpak AS with 95:5:0.05 hexane/ethanol/diethylamine, a flow rate of 1 mL/min. and UV detection at 227 nm. Retention times were 15.5 minutes for the (+)-enantiomer and 21.0 minutes for the (−)-enantiomer.

EXAMPLE 8

(2R,3R,4S)-(+)-2-(4-methoxyphenyl)-4-(1,3-benzodioxol-5-yl)-1-(N,N-di(n -butyl)aminocarbonylm-ethyl)pyrrolidine-3-carboxylic acid A mixture of EXAMPLE 7 (20 g) in ethyl acetate (150 mL) and 5% aqueous sodium bicarbonate was stirred at 25° C. until the salt dissolved and gas evolution stopped. The organic layer was isolated and concentrated. The concentrate was treated with acetonitrile (200 mL), concentrated to 100 mL, cooled to 10° C., treated with diisopropylethylamine (11.8 mL) and EXAMPLE 1 (10.5 g), stirred for 12 hours and concentrated. The concentrate was treated with ethanol (200 mL), concentrated to 100 mL, treated with 40% aqueous NaOH (20 mL), stirred at 60° C. for 4 hours, cooled, poured into water (400 mL), washed with hexanes (2×50 mL then 2×20 mL), treated with ethyl acetate (400 mL) and adjusted to pH 5 with concentrated HCl (12 mL). The organic layer was isolated and concentrated.

EXAMPLE 9

A mixture of 5-((E)-2-nitroethenyl)-1,3-benzodioxole (11.6 g), ethyl 3-(4-methoxyphenyl)-3-oxopropanoate (13.4 g) and sodium ethoxide (5 mg) in tetrahydrofuran (59 g) at 23° C. was stirred for 3 hours, treated with sodium ethoxide (5 mg portions) over 3 hours, mixed with Raney nickel (11.5 g (water-wet and washed with tetrahydrofuran (11.4 g)), tetrahydrofuran (30.6 g), and acetic acid (3.63 g), stirred at 60° C. for 4 hours, cooled to 45° C., treated with trifluoroacetic acid (8.43 g), heated at 60° C. for 2 hours, cooled to 25° C., and filtered. The filtrate was treated with isopropyl acetate (72 g) and adjusted to pH greater than 9 with 25% aqueous potassium carbonate (97 g). The organic layer was isolated, washed twice with 25% aqueous sodium chloride (100 g), and distilled to 30 mL. If the water content (Karl Fisher) of the concentrate was greater than 0.2%, additional isopropyl acetate was added, and the distillation was repeated. The concentrate was treated with isopropyl acetate (8.6 g) and 1,8-diazabicylco[5.4.0]undec-7-ene (7.6 g), stirred at 105° C. for 6 hours, cooled to 20° C., treated with isopropyl acetate (43 g), water (69 g), and activated charcoal (600 mg), stirred for 15 minutes, and filtered. The filtrate was washed with water (69 g) and 3% aqueous sodium chloride (69 g) at 25° C. and with aqueous phosphoric acid (57 g) at 45-60° C., cooled, adjusted to pH greater than 9.5 with 33.3% aqueous potassium carbonate (57 g), and extracted with isopropyl acetate. The extract was concentrated at 60° C. and treated with acetonitrile (10 g) with repetition of this step four times. The concentrate was treated with acetonitrile (54 g) and filtered. The filtrate was treated with (S)-(+)-mandelic acid (2.59 g) in acetonitrile (13.9 g), cooled to 5° C., stirred for 2 hours, and filtered. A mixture of the filtrant and acetonitrile (152 g) was heated at reflux until homogeneous, cooled over 3 hours to 10° C., stirred for 1 hour at 10° C., and filtered. The filtrant was washed with acetonitrile (12 g) and dried at 50° C. for 60 hours. A mixture of the dried filtrant (10 g) and THF (47 g) at 25° C. was treated with 20% aqueous potassium carbonate (30 g) and stirred for 1 hour. The organic layer was isolated, treated with 5.5% aqueous sodium bicarbonate (45.5 g) and EXAMPLE 1 (5.74 g), heated at reflux until not more than 0.5% unreacted starting material remained, and cooled to 25° C. The organic layer was isolated, treated with ethanol (6.4 g) and 14.4% aqueous sodium hydroxide (11.7 g), stirred at reflux until not more than 1% unreacted starting material remained, cooled to 25° C., treated with water (39 g), adjusted to pH 7-10 with 10% aqueous hydrochloric acid, treated with ethyl acetate (55 g), and adjusted to pH 5-6 with 10% aqueous hydrochloric acid. The organic layer was isolated, concentrated at 50° C. to 20 mL, treated with ethyl acetate (30 g), concentrated at 50° C. to 20 mL with repetition of this step until the water content (Karl Fisher) of the concentrate was not more than about 0.4% and filtered.

Substantially chemically and diastereomerically pure atrasentan hydrochloride can be made by reacting substantially chemically and diastereomerically pure atrasentan and an HCl source such as HCl gas, HCl in water, 1,4-dioxane, a solvent having formula $R^6C(O)OR^7$ such as ethyl acetate, or a combination thereof.

Atrasentan Hydrochloride Crystalline Form 3 having substantial crystalline purity 30 was prepared by mixing Atrasentan Hydrochloride Crystalline Form 1 or Form 2, in which the Atrasentan Hydrochloride Crystalline Form 1 or Form 2 was partially soluble in the acetonitrile or the acetone at 40° C. for 14 days.

Atrasentan Hydrochloride Crystalline Form 3 having substantial crystalline purity was prepared by mixing Atrasentan Hydrochloride Crystalline Form 1 or Form 2, in 35 which the Atrasentan Hydrochloride Crystalline Form 1 or Form 2 was partially soluble in the acetonitrile or the acetone at 60° C. for 7 days.

Atrasentan Hydrochloride Crystalline Form 3 may be characterized by powder diffraction data, single crystal data, or a combination thereof.

A sample of Atrasentan Hydrochloride Crystalline Form 3 for powder diffraction analysis was applied as a thin layer, with no prior grinding, to the analysis well of a Scintag×2 Diffraction Pattern System having the following parameters: x-ray source: Cu-Kα; range: 2.00°-40.000° 2θ; scan rate: 1.00 degree per minute; step size: 0.02°; temperature: about 25° C.; wavelength: 1.54178 Å (Cu-Kα).

Atrasentan Hydrochloride Crystalline Form 3 is characterized by a powder diffraction pattern with peaks having respective 2θ values of about 6.7° and 21.95° and at least one peak having a respective 2θ value of about 8.4°, 15.6°, 18.0°, 18.5°, 19.8° or 20.6°, when measured at about 25° C. with Cu-Kα radiation.

It is meant to be understood that peak heights may vary and will be dependent on variables such as the temperature, size of crystal size or morphology, sample preparation, or sample height in the analysis well of the Scintag×2 Diffraction Pattern System.

It is also meant to be understood that peak positions may vary when measured with different radiation sources. For example, Cu-Kα$_1$, Mo-Kα, Co-Kα and Fe-Kα radiation, having wavelengths of 1.54060 Å, 0.7107 Å, 1.7902 Å and 1.9373 Å, respectively, may provide peak positions that differ from those measured with Cu-Kα radiation.

The term "about" preceding a series of peak positions is meant to include all of the peak positions of the group which it precedes.

The term "about" preceding a series of peak positions means that all of the peaks of the group which it precedes are reported in terms of angular positions with a variability of ±0.1° or ±0.01°.

Accordingly, for example, the phrase about 6.7° and 21.95° and about 8.4°, 15.6°, 18.0°, 18.5°, 19.8° or 20.6° means about 6.7° and about 21.95° and about 8.4°, about 15.6°, about 18.0°, about 18.5°, about 19.8° or about 20.60° or 6.7°±0.1 and 21.95°±0.01 and about 8.4°±0.1, 15.6°±0.1, 18.0°±0.1, 18.5°±0.1, 19.8°°±0.1 or 20.6°±0.1.

Peak positions may also be expressed with a variability which accounts for differences between powder x-ray diffractometers, variability between Cu-Kα radiation sources, variability from sample to sample on the same diffractometer, and differences in sample heights in the analysis well. This variability is preferably expressed ±0.1°.

Atrasentan Hydrochloride Crystalline Form 3 is an endothelin receptor antagonist and is useful for prevention or treatment of diseases or inhibition of adverse physiological events caused or exacerbated by up-regulation or over-expression of endothelin.

The term "adverse physiological events," as used herein, means bone metastases, bone turnover, metastatic growth, new metastatic growth and net bone loss in patients having breast, colon, kidney, ovarian or prostate cancer.

The term "disease," as used herein, means cancer, fibrotic diseases, nociception, restenosis and stenosis, wherein cancer includes bladder, breast, colon, lung, ovarian, prostate, multiple myeloma and osteosarcoma, fibrotic disease includes cystic fibrosis, lung fibrosis and liver cirrhosis, nociception includes cancer-related pain and bone pain associated with bone cancer, restinosis includes restinosis following arterial injury, and stenosis includes pathogenic stenosis of blood vessels.

Use of atrasentan hydrochloride for treating bone pain associated with bone cancer is demonstrated in commonly-owned PCT Application No. PCT/US01/24716, published as WO 02/11713 A2.

Use of endothelin receptor antagonists for treating cancer is demonstrated in Journal of Clinical Investigation Vol. 87 1867 (1991).

Use of endothelin receptor antagonists for treating breast cancer is demonstrated in Int. J. Oncol. 2005 April; 26(4): 951-960.

Use of endothelin receptor antagonists for treating cancer is demonstrated in Journal of Clinical Investigation Vol. 87 1867 (1991).

Use of endothelin receptor antagonists for treating cancer-related pain is demonstrated in WO 02/11713 A2.

Use of endothelin receptor antagonists for treating colon cancer that has metastasized to bone is described in Nature Medicine Vol 1 No. 9 September 1995.

Use of endothelin receptor antagonists for treating cystic fibrosis is demonstrated in European Respiratory Journal. Vol. 13(6):1288-92 (1999).

Use of endothelin receptor antagonists for treating liver cirrhosis is demonstrated in Gut Vol. 53(3): 470-471 (2004).

Use of endothelin receptor antagonists for treating lung fibrosis is demonstrated in Lancet Vol. 341(8860): 1550-1554 (2004).

Use of endothelin receptor antagonists for treating nociception is demonstrated in Journal of Pharmacology and Experimental Theraputics Vol. 271, 156 (1994).

Use of endothelin receptor antagonists for treating prostate cancer is demonstrated in WO 02/11713 A2.

Use of endothelin receptor antagonists for treating restenosis is demonstrated in Canadian Journal of Cardiology 19 No. 8: 902-906 (2003).

Use of endothelin receptor antagonists for treating stenosis is demonstrated in Chest Vol. 125(2): 390-396 (2004).

Use of endothelin receptor antagonists for inhibiting bone metastases, bone turnover, metastatic growth or net bone loss is demonstrated in WO 02/11713 A2.

Use of endothelin receptor antagonists for preventing new metaststic growth is demonstrated in WO 02/11713 A2.

The avidity of human cancers for bone, the resulting tumor burden to bone and bone pain resulting therefrom and the bi-directional interactions between tumor cells, osteoclasts and tumor growth and the new bone metastases to bone resulting therefrom are demonstrated in Nature Reviews Cancer 2, 584-593 (2002).

The role of endothelin in ovarian cancer is described in American Journal of Pathology 1998; 153: 1249-1256.

Compositions made with or comprising Atrasentan Hydrochloride Crystalline Form 3 may be administered, for example, bucally, ophthalmically, orally, osmotically, parenterally (intramuscularly, intrasternally, intravenously, subcutaneously), rectally, topically, transdermally, or vaginally. Ophthalmically administered dosage forms may be administered as, for example, elixirs, emulsions, microemulsions, oinments, solutions, suspensions, or syrups. Orally administered solid dosage forms may be administered as, for example, capsules, dragees, emulsions, granules, pills, powders, solutions, suspensions, tablets, microemulsions, elixirs, syrups, or powders for reconstitution. Osmotically and topically administered dosage forms may be administered as, for example, creams, gels, inhalants, lotions, ointments, pastes, or powders. Parenterally administered dosage forms may be administered, as, for example, aqueous or oleaginous suspensions. Rectally and vaginally dosage forms may be administered, for example, as creams, gels, lotions, ointments, or pastes.

The therapeutically acceptable amount of Atrasentan Hydrochloride Crystalline Form 3 depends on recipient of treatment, disorder being treated and severity thereof, composition containing it, time of administration, route of administration, duration of treatment, its potency, its rate of clearance and whether or not another drug is co-administered. The amount of Atrasentan Hydrochloride Crystalline Form 3 used to make a composition to be administered daily to a patient in a single dose or in divided doses is from about 0.03 to about 200 mg/kg body weight. Single dose compositions contain these amounts or a combination of submultiples thereof.

Atrasentan Hydrochloride Crystalline Form 3 may be administered with or without an excipient and with or without at least one additional chemotherapeutic agent. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, processing aids, releasing agents, shell excipients, sterilizing agents, sweeteners, solubilizers, wetting agents and mixtures thereof.

Excipients for preparation of compositions made with or comprising Atrasentan Hydrochloride Crystalline Form 3 to be administered orally in solid dosage forms include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, FD&C Yellow No. 6, fractionated coconut oil, gelatin such as Gelatin Type 195, germ oil, glucose, glycerol, glycerin, groundnut oil, hydroxypropylmethyl celluose, isopropanol, isotonic saline, lactose, lecithin, magnesium hydroxide, magnesium stearate, malt, mannitol, monoglycerides, olive oil, peanut oil, phosphatidylcholine, polyethylene glycol 600, propylene glycol, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, Sorbitol Special (sorbitol, sorbitol anhydrides and mannitol), soybean oil, stearic acids, stearyl fumarate, sucrose, surfactants, talc, tragacanth, tetrahydrofurfuryl alcohol, titanium dioxide, triglycerides, water, and mixtures thereof. Excipients for preparation of compositions made with Atrasentan Hydrochloride Crystalline Form 3 to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions made with Atrasentan Hydrochloride Crystalline Form 3 to be administered osmotically include, for example, chlorofluorohydrocarbons, ethanol, water and mixtures thereof. Excipients for preparation of compositions made with Atrasentan Hydrochloride Crystalline Form 3 to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions made with or comprising Atrasentan Hydrochloride Crystalline Form 3 to be administered rectally or vaginally include, for example, cocoa butter, polyethylene glycol, wax and mixtures thereof.

Additional chemotherapeutic agents include, but are not limited to, therapeutically acceptable amounts of radiation such as γ-radiation or compounds such as (N-(2-((4-hydroxyphenyl)amino)pyrid-3-yl)-4-methoxybenzenesulfonamide, N-Ac-Sar-Gly-Val-D-alloIle-Thr-Nva-Ile-Arg-Pro-NHCH$_2$CH$_3$ or a salt thereof, actinomycin D, AG13736, 17-allylamino-17-demethoxygeldanamycin, 9-aminocamptothecin, N-(4-(3-amino-1H-indazol-4-yl)phenyl)-N'-(2-fluoro-5-methylphenyl)urea or a salt thereof, N-(4-(4-aminothieno[2,3-d]pyrimidin-5-yl)phenyl)-N'-(2-fluoro-5-(trifluoromethyl)phenyl)urea or a salt thereof, anastozole, AP-23573, asparaginase, azacitidine, bevacizumab, bicalutamide, bleomycin a2, bleomycin b2, bortezamib, busulfan, campathecins, carboplatin, carmustine (BCNU), CB1093, cetuximab, chlorambucil, CHIR258, cisplatin, CNF-101, CNF-1001, CNF-2024, CP547632, crisnatol, cytarabine, cyclophosphamide, cytosine arabinoside, daunorubicin, dacarbazine, dactinomycin, dasatinib, daunorubicin, deferoxamine, demethoxy-hypocrellin A, depsipeptide, dexamethasone, 17-dimethylaminoethylamino-17-demethoxygeldanamycin, docetaxel, doxifluridine, doxorubicin, EB1089, eothilone D, epirubicin, 5-ethynyl-1-β-D-ribofuranosylimidazole-4-carboxamide (EICAR), erlotinib, etoposide, everolimus, 5-fluorouracil (5-FU), floxuridine, fludarabine, flutamide, gefitinib, geldanamycin, gemcitabine, goserelin, N-(2-(4-hydroxyanilino)-3-pyridinyl)-4-methoxybenzenesulfonamide or a salt thereof, hydroxyurea, idarubicin, ifosfamide, imatinab, interferon-a, interferon-γ, IPI-504, irinotecan, KH 1060, lapatanib, LAQ824, leuprolide acetate, letrozole, lomustine (CCNU), lovastatin, megestrol, melphalan, mercaptopurine, methotrexate, 1-methyl-4-phyenylpyridinium, MG132, mitomycin, mitoxantrone, MLN-518, MS-275, mycophenolic acid, mytomycin C, nitrosoureas, oxaliplatin, paclitaxel, peplomycin, pheuretinide, photosensitizer Pc4, phtalocyanine, pirarubicin, plicamycin, prednisone, procarbizine, PTK787, PU24FCl, PU3, radicicol, raloxifene, rapamycin, ratitrexed, ribavirin, rituximab, sorafenib, staurosporine, suberoylanilide hydroxamic acid, sunitinib, tamoxifen, taxol, temozolamide, temsirolimus, teniposide, thapsigargin, thioguanine, thrombospondin-1, tiazofurin, topotecan, trapoxin, trastuzumab, treosulfan, trichostatin A, trimetrexate, trofosfamide, tumor necrosis factor, valproic acid, VER49009, verapamil, vertoporfin, vinblastine, vincristine, vindesine, vinorelbine vitamin D3, VX-680, zactima, ZK-EPO, zorubicin or combinations thereof.

Treatment or prevention of cancer with a therapeutically effective amount of Atrasentan Hydrochloride Crystalline Form 3 may also comprise administering radiation therapy with at least one chemotherapeutic agent to a patient whose the cancer is not refractory. Treatment or prevention of cancer with a therapeutically effective amount of Atrasentan Hydrochloride Crystalline Form 3 may also comprise administering radiation therapy with at least one chemotherapeutic agent to a patient whose the cancer is refractory. Treatment or prevention of cancer may also comprise administering a therapeutically effective amount of Atrasentan Hydrochloride Crystalline Form 3, with or without radiation and with or without a therapeutically effective amount of at least one additional chemotherapeutic agent to a patient who has undergone surgery for treatment of cancer. Treatment or prevention of cancer may also comprise administering a therapeutically effective amount of Atrasentan Crystalline Form 3 to a patient whose cancer is refractory to treatment with a chemotherapy and/or radiation therapy. The therapeutically effective amount of Atrasentan Crystalline Hydrochloride Form 2 may administered concurrently with chemotherapy or radiation therapy or prior to or subsequent to chemotherapy or radiation therapy.

Other diseases or conditions of bone resulting in net bone loss that may be treated with a therapeutically effective amount of Atrasentan Crystalline Hydrochloride Form 3 include, but are not limited to, post-menopausal osteoporosis, ovariectomy patients, senile osteoporosis, results from long-term treatment withcorticosteroids, side effects from glucocorticoid or steroid treatment, Cushings's syndrome, gonadal dysgenesis, periarticular erosions in rheumatoid arthritis, osteoarthritis, Paget's disease, osteohalisteresis, osteomalacia, hypercalcemia of malignancy, osteopenia due to bone metastases, periodontal disease, hyperparathyroidism, osteroperosis from Lupron therapy, and starvation. All of these conditions are characterized by bone loss resulting from an imbalance between the degradation of bone (bone resorption) and the formation of new healthy bone. This turnover of bone continues normally throughout life and is the mechanism by which bone regenerates. However, these conditions will tip the balance towards bone loss such that the amount of bone resorbed is inadequately replaced with new bone, resulting in net bone loss.

Accordingly, a therapeutically effective amount of Atrasentan Hydrochloride Crystalline Form 3 may be administered to a patient having net bone loss along with a therapeutically effective amount of a compound that inhibits net bone loss such as, for example, a bisphosphonate such as, for example, alendronate (Fosamax®), etidronate (Didrocal®) and risedronate (Actonel®), hormone replacement therapy (HRT), ipriflavone, vitamin D$_3$ or tetracycline and flurbiprofen.

The foregoing is meant to be illustrative of the invention and not meant to limit it to disclosed embodiments. Variations and changes obvious to one skilled in the art are intended to be within the scope and nature of the invention as defined in the appended claims.

What is claimed is:

1. Atrasentan Hydrochloride Crystalline Form 3 characterized, when measured at about 25° C. with Cu-Kα radiation, by a powder diffraction pattern with peaks having respective 2θ values of about 6.7°, 8.4°, 15.6°, 18.0°, 18.5°, 19.8°20.6° and 21.95°.

* * * * *